United States Patent [19]

Orimo et al.

[11] Patent Number: 4,822,817

[45] Date of Patent: Apr. 18, 1989

[54] REMEDY FOR BONE DISEASE

[75] Inventors: Hajime Orimo, Tokyo; Norihiro Kakimoto, Machida; Kohei Miyao, Tokyo, all of Japan

[73] Assignee: Asai Germanium Research Institute, Tokyo, Japan

[21] Appl. No.: 58,278

[22] Filed: Jun. 4, 1987

[30] Foreign Application Priority Data

Jun. 18, 1986 [JP] Japan .................................. 61-142198

[51] Int. Cl.⁴ ..................... A61K 31/32; A61K 31/28
[52] U.S. Cl. .................................................... 514/492
[58] Field of Search ........................... 556/83; 514/492

[56] References Cited

U.S. PATENT DOCUMENTS

| | | | |
|---|---|---|---|
| 3,812,167 | 5/1974 | Pahk | 556/83 |
| 4,420,430 | 12/1983 | Chang et al. | 556/83 |
| 4,508,654 | 4/1985 | Chang et al. | 556/83 |

FOREIGN PATENT DOCUMENTS

| | | | |
|---|---|---|---|
| 55-105696 | 8/1980 | Japan | 556/83 |
| 57-203090 | 12/1982 | Japan | 556/492 |
| 203090 | 12/1982 | Japan | 514/492 UX |
| 58-146507 | 9/1983 | Japan | 556/83 |
| 59-184193 | 10/1984 | Japan | 556/83 |
| 61-145116 | 2/1986 | Japan | 556/492 |
| 145116 | 7/1986 | Japan | 514/492 UX |
| 1365997 | 9/1974 | United Kingdom | 514/492 |
| 2158070 | 11/1985 | United Kingdom | 514/492 |

*Primary Examiner*—Paul F. Shaver
*Attorney, Agent, or Firm*—Burns, Doane, Swecker & Mathis

[57] ABSTRACT

This invention provides remedies for bone diseases characterized by comprising organogermanium compounds expressed by the following formula:

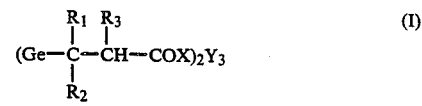

(wherein $R_1$, $R_2$ and $R_3$ respectively denote a hydrogen atom, a lower alkyl group such as a methyl or ethyl group, or a substituted or non-substituted phenyl group; X denotes a hydroxyl, O-lower alkyl or amino group; and Y denotes an oxygen or sulfur atom) as an effective ingredient. These remedies are effect for the remedy of osteoporosis.

9 Claims, 3 Drawing Sheets

REMEDY FOR BONE DISEASE

BACKGROUND OF THE INVENTION

The present invention relates to remedies for bone diseases, and particularly to strong remedies for bone diseases containing organogermanium compounds as effective ingredients.

Recently, metabolic bone diseases such as senile osteoporosis and renal osteodystrophy, which are due to calcium metabolism or other causes related thereto, have been increasing. In addition, such diseases have become a matter of great concern in the medical field because the pathologic physiology of the above-described metabolic bone diseases and analytical methods concerned therewith which were unknown heretofore have been established.

It is generally said that the above-described bone diseases are closely related to calcium metabolism and abnormalities thereof. For example, it is thought that senile osteoporosis is caused by a decrease in osteogenesis compared with bone resorption produced by an imbalance between osteogenesis and bone resorption due to combinations of calcium metabolism and other factors.

Since this sort of disease however creates pain which is generally difficult to counteract with usual analgesics or is accompanied with illnesses in which bones easily break and are difficult to mend, a rapid remedy is required.

Since the above-described metabolic bone diseases are, however, not a single disease but a general term for a particular pathology and their causes have not yet been determined, or various views about their origins have been advanced, there are problems with respect to the difficulty in establishing therapeutics and remedies for such bone diseases.

On the other hand, although calcitonon and active vitamin D have been recently developed as a remedy for metabolic bone diseases, their effects cannot be said to be strong and they have disadvantages in that they have strong side-effects and are difficult to use.

SUMMARY OF THE INVENTION

The present invention has been achieved against the background of the situation described above, and is characterized by comprising organogermanium compounds expressed by the following formula:

$$(Ge-\underset{\underset{R_2}{|}}{\overset{\overset{R_1}{|}}{C}}-\overset{\overset{R_3}{|}}{C}H-COX)_2Y_3 \quad (I)$$

(wherein $R_1$, $R_2$ and $R_3$ respectively denote a hydrogen atom, a lower alkyl group such as a methyl or ethyl group, or a substituted or non-substituted phenyl group; X denotes a hydroxyl, O-lower alkyl or amino group; and Y denotes an oxygen or sulfur atom) as an effective ingredient.

In other words, the inventors have investigated in detail the pathology and the origins of the above metabolic bone diseases, have noticed organogermanium compounds and have thought of an effective therapeutic for such diseases, utilizing these compounds for the purpose of, for example, ameliorating the imbalance between osteogenesis and bone resorption. Therefore, the inventors have energetically researched into usable compounds, resulting in the achievement of the present invention.

DETAILED DESCRIPTION OF THE INVENTION

Germanium (Ge), which is a known metal, is conventionally an object of investigation in the fields of physics and inorganic chemistry. Investigations into organic compounds of germanium have recently proceeded and the results of these investigations have been actively reported, and consequently these organic compounds have attracted attention in various technical fields.

For example, it is becoming well known in the field of pharmaceutics that carboxyethylgermanium sesquioxide ($GeCH_2CH_2COOH)_2O_3$, which is an organogermanium compound and in which propionic acid derivatives of germanium and oxygen atoms are bonded in a ratio of 2:3, exhibits the effects of reducing blood pressure and amiloyd degeneration, produces excellent physiological reactions such as the activation of macrophages and has an antitumor effect obtained by inducing interferons, but exhibits no toxicity and side-effects at all, and this compound is being clinically tested.

Since the remedies for bone diseases of the present invention contain the organogermanium compounds shown in the above Formula I as effective ingredients, these compounds are first described below. The basic skeletons of these compounds are germyl propionic acid in which propionic acid derivatives having three substituents $R_1$ to $R_3$ and oxygen functional groups OX in molecules are bonded to germanium atoms. The germanium atoms in these basic skeletons are bonded to oxygen atoms (when Y=O) or sulfur atoms (when Y=S) in the ratio of 2:3.

In these compounds, the substituents $R_1$, $R_2$ and $R_3$ respectively denote a hydrogen atom, a lower alkyl group such as a methyl, ethyl, propyl or butyl group, or a substituted or non-substituted phenyl group; and the substituent X denotes a hydroxyl, O-lower alkyl, or amino group.

In addition, the substituents $R_1$ and $R_2$ are bonded at the $\alpha$-position relative to the germanium atom and the substituent $R_3$ is bonded at the $\beta$-position relative to the same. Therefore, examples of organogermanium compounds used as remedies of the present invention include the following compounds:

$$(Ge-CH_2-CH_2-COOH)_2O_3 \quad (I1)$$

$$(Ge-\overset{\overset{CH_3}{|}}{C}H-CH_2-COOH)_2O_3 \quad (I2)$$

$$(Ge-CH_2-\overset{\overset{CH_3}{|}}{C}H-COOH)_2O_3 \quad (I3)$$

$$(Ge-\overset{\overset{CH_3}{|}}{\underset{\underset{CH_3}{|}}{C}H}-CH-COOH)_2O_3 \quad (I4)$$

$$(Ge-\overset{\overset{CH_3}{|}}{\underset{\underset{CH_3}{|}}{C}}-CH_2-COOH)_2O_3 \quad (I5)$$

$$(Ge-\underset{\underset{C_6H_5}{|}}{C}H-CH_2-COOH)_2O_3 \quad (I6)$$

-continued

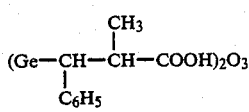 (I7)

(Ge—CH₂—CH₂—COOCH₃)₂O₃ (I8)
(Ge—CH₂—CH₂—CONH₂)₂O₃ (I9)
(Ge—CH₂—CH₂—COOH)₂S₃ (I10)

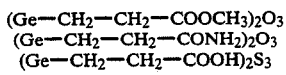 (I11)

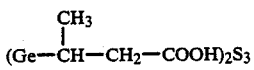 (I12)

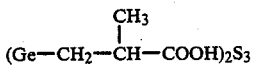 (I13)

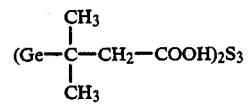 (I14)

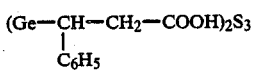 (I15)

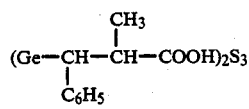 (I16)

(Ge—CH₂—CH₂—COOCH₃)₂S₃ (I17)
(Ge—CH₂—CH₂—CONH₂)₂S₃ (I18)

The organogermanium compounds having the above-described structures can be produced by various methods.

For example, when X=OH and Y=O in the above-described formula I, a trihalogermyl propionic acid such as trichlorogermyl propionic acid (1) in which the substituents $R_1$ to $R_3$ have been previously introduced may be hydrolyzed, as shown in the following reaction formula 1:

Reaction Formula 1

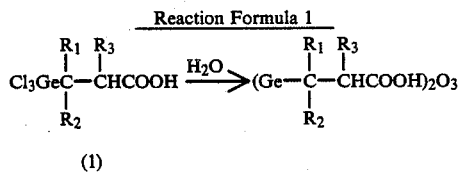

(1)

When X=OH and Y=S in the above formula I, a trihalogermyl propionic acid such as the above trichlorogermyl propionic acid (1) may be reacted with hydrogen sulfide H₂S, as shown in the following reaction formula 2:

Reaction Formula 2

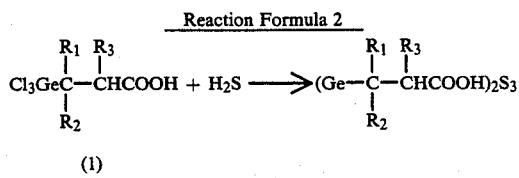

(1)

On the other hand, when X=O-lower alkyl group in the formula I, for example, the above-described compound (1) may be reacted with thionyl chloride to be changed into the corresponding acid halide which may then be reacted with the alcohol corresponding to the above lower alkyl group and subsequently with hydrogen sulfide, and which may then be reacted with ammonia and subsequently with hydrogen sulfide when X=NH₂ in the formula I.

The results of the instrumental analyses such as the nuclear magnetic resonance (NMR) and the infrared absorption (IR) spectra of the organogermanium compounds obtained in the above-mentioned methods support well the fact that these compounds are those expressed by the formula I. Remedies for bone diseases of the present invention contain organogermanium compounds synthesized by the above-mentioned methods as effective ingredients. No difficulty will be experienced in their administration in either oral or parenteral form, but in the case of oral administration it is possible to utilize conventionally-used forms such as tablets, capsules, powder or granules.

EFFECT AND FUNCTION OF THE INVENTION

Osteoblasts which are important for bone diseases are cells arranged to form a monolayer cylinder on the surface of osteogenesis and are said to synthesize organic substrates such as collagen and glycoproteins and to form substrate vesicles so as to deposit bone salts such as hydroxyapatite therein. When the remedies of the present invention were allowed to act on these osteoblasts, the effect of direct activation was recognized.

In addition, since the concentration of the compounds required for the above-described effect to be exhibited is extremely low, combined with the low toxicity of the organogermanium compounds per se, it can be said that the remedies of the present invention are strong and safe. The remedies can therefore ameliorate the imbalance between osteogenesis and bone resorption and be used for remedying osteoporosis.

When the remedies of the present invention were actually administered to patients with osteoporosis and their effect on bone metabolism was investigated by measuring the bone-salt content of left radius, a significant difference was observed between the test group and a control group and it was confirmed that the remedies of the present invention were effective for the remedy of osteoporosis.

DESCRIPTION OF EXAMPLES

Figure 1:
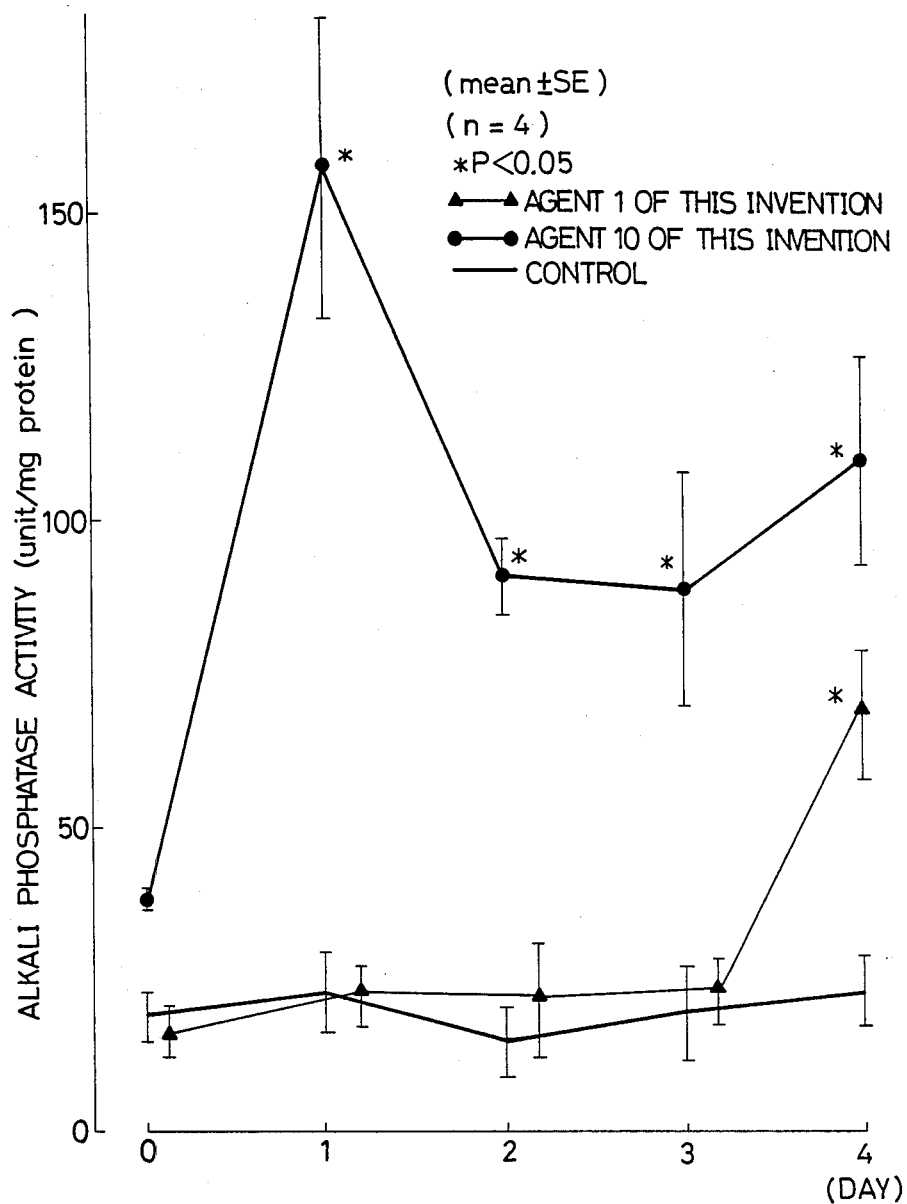
FIG. 1 is a graph showing the feature of activation of cloned osteoblasts by remedies of the present invention.

The present invention is described in detail below with reference to Experimental Examples and Examples.

EXPERIMENTAL EXAMPLE 1

Synthesis 1 of Organogermanium Compound 500 ml of water was added to 50.4 g (0.2 mol) of trichlorogermyl propionic acid and the mixture was agitated for 1 hour and then allowed to stand for 24 hours. The separated crystals were filtered and recrystallized from water to obtain 28.0 g of Compound I1. The values of the physical properties of Compound I1 obrtained corresponded with the values reported in literature.

The other compounds were produced in accordance with the methods described, for example, in Japanese Patent Laid-Open No. 226592/1985.

EXPERIMENTAL EXAMPLE 2 synthesis 2 of Organogermanium Compound 25.2 g (0.1 mol) of trichlorogermyl propionic acid was dissolved in 200 ml of anhydrous benzene and 2.4 g (0.1 mol) of anhydrous pyridine was added to the resulting solution. The mixture obtained was agitated and a dried hydrogen sulfide gas was passed therethrough for 60 minutes. Benzene was removed from the mixture with attention being paid to the oil substance produced which was then dissolved in methanol. 300 ml of purified water was added to the solution obtained and the separated crystals were recrystallized from methanol to obtain 17.1 g of Compound I10. The values of the physical properties of Compound I10 obtained corresponded with the values reported in literature.

The other compounds were produced in accordance with the methods described, for example, in Japanese Patent Laid-Open No. 35916/1984.

EXAMPLE 1

Examination 1 of Pharmaceutical Effect (Method)

Clone MC3T3-E1 cells obtained from new born mouse calvaria was used as cultivation osteoblasts. The osteoblasts were sown in α-MEM containing 10% fetal calf serum so as to become $10^5$/dish and cultivated under the conditions of 37° C. and 95% air/5% $CO_2$ until they reached a confluent state.

The effects of remedies of the present invention were examined by adding the remedies respectively containing as an effective ingredient Compounds I1 to I18 into α-MEM containing 0.3% BSA so that the final concentration of these compounds became 10 μg/ml.

Alkaline phosphatase was used as an index of the activation of osteoblasts and measured after cultivation for 1 to 4 days.

(Result)

By adding the remedies of the present invention, as shown in FIG. 1, the alkaline phosphatase activity of MC3T3-E1 reached a peak after cultivation for 4 days when Compound I1 was used as a main ingredient (Agent 1 of this invention), and it reached a peak after cultivation for 1 day when Compound I10 was used as a main ingredient (Agent 10 of this invention), with a significant difference being recognized between the respective agents and a control sample.

It was confirmed from the above-described facts that the remedies of the present invention were able to increase the activity of cloned osteoblasts. In addition, when the remedies of the present invention containing the other compounds as effective ingredients were used, the results obtained were substantially the same as those described above.

Figure 2:
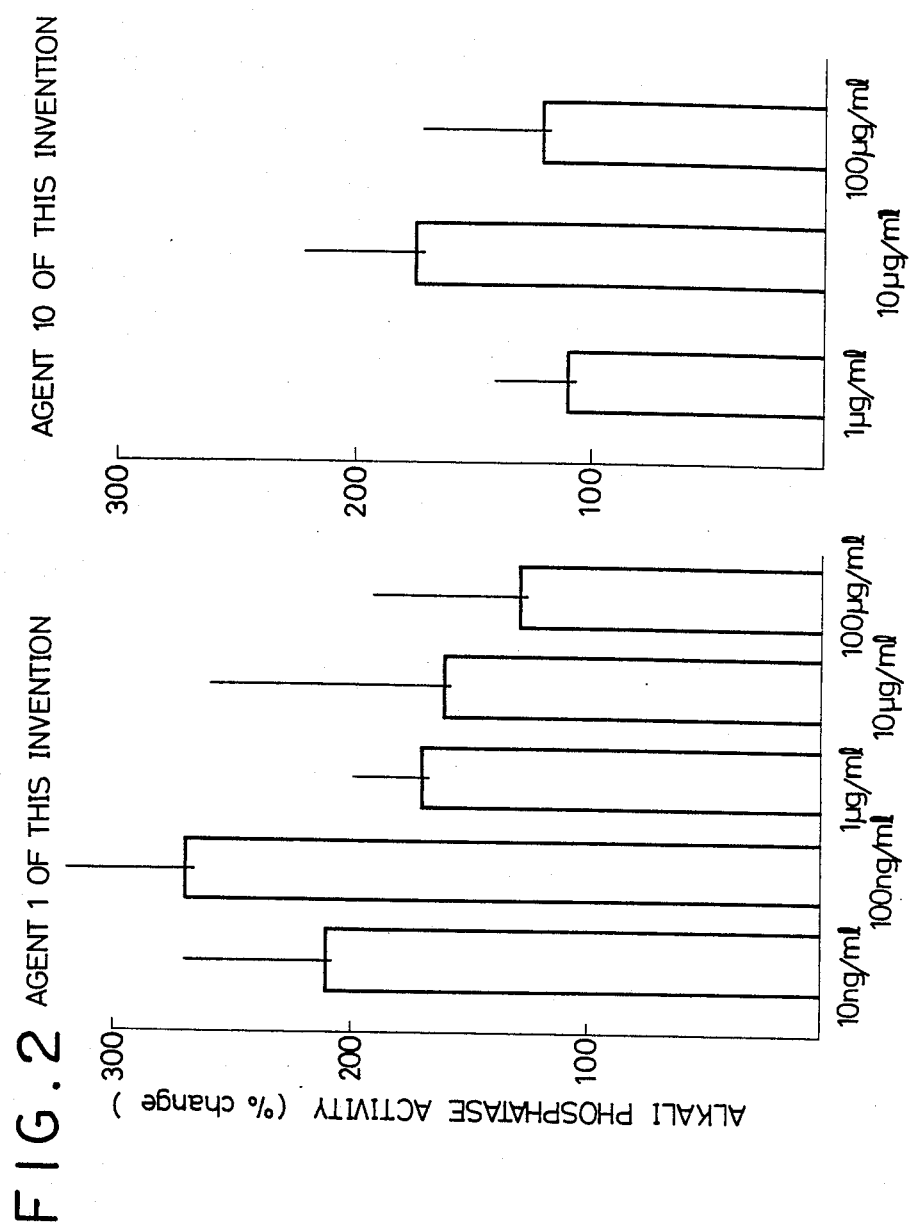
FIG. 2 is a graph showing the feature of dose response of remedies of the prsent invention.

Since the alkaline phosphatase activity reached a peak after culivation for 4 days and 1 day in the cases of Agents 1 and 10 of this invention, respectively, the investigation of the dose response of each case clarified that Agents 1 and 10 of this invention exhibited the required effect at concentrations of as low as 100 ng/ml and 10 μg/ml, respectively, as shown in FIG. 2.

EXAMPLE 2

Examination 2 of Pharmaceutical Effect

Six capsules of the agent of this invention containing 250 mg of Compound I1 as a main ingredient were administered to eight patients suffering from osteoporosis (all patients being female; average age: 72 years old±4 years) for 12 months and the bone-salt content of the left radius of each patient was measured before administration started and after 3, 6, 9 and 12 months had passed.

Figure 3:
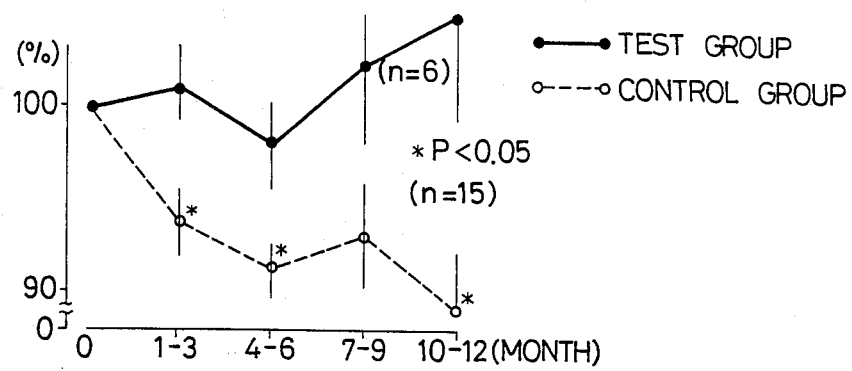
FIG. 3 is a graph showing that remedies of the present invention can prevent the reduction of the bone-salt content of the left radius.

As seen from FIG. 3, the results obtained clarified that the bone-salt content of the left radius in a group to which no agent was administered gradually reduced during the time of observation over the period of 12 months, while the reduction of the content in a group to which the agent of this invention was administered was significantly inhibited.

A significant difference of P 0.05 was found at each of the measurements after 3, 6 and 12 months.

Figure 4:
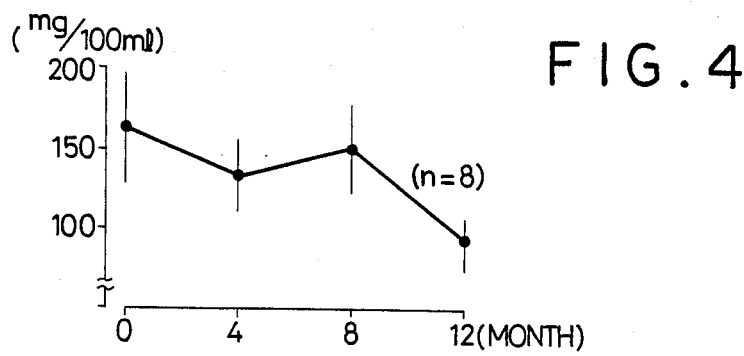
FIG. 4 is a graph showing that remedies of the present invention can reduce A1-Pase in blood.
Figure 5:
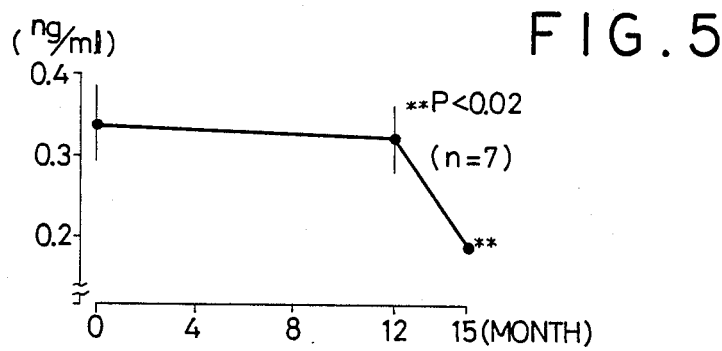
FIG. 5 is a graph showing that remedies of the present invention can reduce iPTH in blood.

In addition, it was found that A1-Pase in blood and iPTH in blood were significántly reduced, as shown in FIGS. 4 and 5, respectively.

A significant difference of $P<0.05$ with respect to iPTH in blood was also found.

We claim:

1. A method for ameliorating the imbalance between osteogenesis and bone resorption, said method comprising administering to an organism in need of such treatment an effective amount to ameliorate the imbalance between osteogenesis and bone resorption of a compound of the formula:

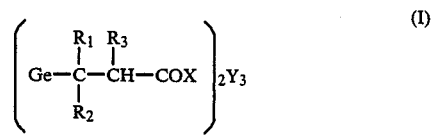

(I)

wherein $R_1$, $R_2$ and $R_3$ are independently selected from a hydrogen atom, a lower alkyl group and a phenyl group; X denotes a hydroxyl, O-lower alkyl or amino group; and Y denotes an oxygen or sulfur atom.

2. The method as claimed in claim 2 wherein the lower alkyl group is a methyl group, an ethyl group, a propyl group or a butyl group.

3. The method as claimed in claim 1 wherein $R_1$, $R_2$ and $R_3$ are each a hydrogen atom.

4. The method as claimed in claim 1 wherein $R_1$, $R_2$ and $R_3$ is a phenyl group.

5. The method as claimed in claim 1 wherein X is a hydroxyl group.

6. The method as claimed in claim 1 wherein Y is an oxygen atom.

7. The method as claimed in claim 6 wherein $R_1$, $R_2$ and $R_3$ are each a hydrogen atom, X is a hydroxyl group and Y is an oxygen atom.

8. The method as claimed in claim 1 wherein Y is a sulfur atom.

9. The method as claimed in claim 8 wherein $R_1$, $R_2$ and $R_3$ are each a hydrogen atom, X is a hydroxyl group and Y is a sulfur atom

* * * * *